US008229547B2

(12) United States Patent  
Rauscher-Scheibe

(10) Patent No.: US 8,229,547 B2
(45) Date of Patent: Jul. 24, 2012

(54) METHOD FOR DETERMINING AND DISPLAYING PERFUSION PARAMETERS IN TOMOGRAPHY

(75) Inventor: Annabella Rauscher-Scheibe, Hamburg (DE)

(73) Assignee: Siemens Aktiengesellschaft, Munich (DE)

( * ) Notice: Subject to any disclaimer, the term of this patent is extended or adjusted under 35 U.S.C. 154(b) by 614 days.

(21) Appl. No.: 12/382,959

(22) Filed: Mar. 27, 2009

(65) Prior Publication Data

US 2009/0247864 A1  Oct. 1, 2009

Related U.S. Application Data

(60) Provisional application No. 61/041,309, filed on Apr. 1, 2008.

(30) Foreign Application Priority Data

Apr. 25, 2008  (DE) .......................... 10 2008 020 814

(51) Int. Cl.
*A61B 6/00* (2006.01)
*A61B 5/05* (2006.01)
*G06K 9/20* (2006.01)
(52) U.S. Cl. ......... 600/431; 600/425; 382/128; 382/131
(58) Field of Classification Search .................. 600/431, 600/41, 428, 420, 407, 410, 425; 378/21, 378/62; 382/128–134; 702/19; 250/363.04
See application file for complete search history.

(56) References Cited

U.S. PATENT DOCUMENTS

| 7,082,180 B2 * | 7/2006 | Edic et al. .......................... 378/4 |
| 7,333,588 B2 * | 2/2008 | Mistretta et al. ................. 378/10 |
| 2006/0083687 A1 * | 4/2006 | Yang .............................. 424/9.3 |

FOREIGN PATENT DOCUMENTS

EP  1537824 A1  6/2005
WO  WO 2005104936 A1  11/2005

* cited by examiner

*Primary Examiner* — Long V. Le
*Assistant Examiner* — Katherine Fernandez
(74) *Attorney, Agent, or Firm* — Harness, Dickey & Pierce, P.L.C.

(57) ABSTRACT

A method is disclosed for determining and displaying perfusion parameters. In at least one embodiment, the method includes measuring an arterial contrast agent profile; measuring a contrast agent profile in a tissue of an organ; temporally synchronizing measured values of the arterial contrast agent profile and the contrast agent profile by interpolation; fitting a theoretical parameterized contrast agent profile to the measured contrast agent profile in the tissue by minimizing the differences between the theoretical and measured contrast agent profiles over a multiplicity of times in a measurement interval by fitting function parameters; and determining at least one perfusion parameter from the function parameters in the case of minimal deviation between the theoretical and measured contrast agent profiles.

26 Claims, 4 Drawing Sheets

METHOD FOR DETERMINING AND DISPLAYING PERFUSION PARAMETERS IN TOMOGRAPHY

PRIORITY STATEMENT

The present application hereby claims priority under 35 U.S.C. §119(e) on U.S. provisional patent application Ser. No. 61/041,309 filed Apr. 1, 2008 and under 35 U.S.C. §119 on German patent application number DE 10 2008 020 814.0 filed Apr. 25, 2008, the entire contents of each of which are hereby incorporated herein by reference.

FIELD

At least one embodiment of the invention generally relates to a method for determining and displaying perfusion parameters in tomography, particularly in computed tomography. For example, it may relate to a method in which a contrast agent bolus comprising a contrast agent is dispensed to a patient while the patient is being scanned by a scanner, tomographic image series are reconstructed from a start time to an end time using absorption data scanned by the scanner, and perfusion parameters relating to the diffusion of the contrast agent bolus are calculated from the image series using numerical modeling.

BACKGROUND

Methods for determining and displaying perfusion parameters in tomography, particularly in computed tomography, are widely known. In the process, conclusions about possible pathological changes of the tissue or an associated organ are drawn from the perfusion behavior of the tissue. To this end, the most diverse developments of the models used, such as the maximum slope model or the Patlak model, exist. Here, scan data is acquired at temporally short intervals, which have lengths which are as equal as possible, and data from the bolus application is also used directly where possible in order to determine perfusion parameters, such as the blood flow, the blood volume, start times, and means transit times, from model calculations using usually very noisy data.

SUMMARY

In at least one embodiment of the invention, an improved method is specified which makes it possible to determine precise perfusion parameters from a few and possibly not temporally equidistant measurements.

This object is achieved by the features of the independent patent claim 1. Advantageous developments of the invention are the subject matter of the dependent claims.

To this end, a method is proposed, in at least one embodiment, for determining and displaying perfusion parameters in tomography, which is improved compared to the prior art, in which a contrast agent bolus comprising a contrast agent is dispensed to a patient while said patient is being scanned by a CT scanner, tomographic image series are reconstructed from a start time to an end time using absorption data scanned by the CT scanner, and perfusion parameters relating to the diffusion of the contrast agent bolus are calculated from the image series using numerical modeling.

According to at least one embodiment of the invention, improvement results from carrying out the following method steps:

measuring a first temporally variable contrast agent concentration in a first arterial region by determining a change in the CT values occurring there over a multiplicity of measurement times and saving it as an arterial contrast agent profile a(t) in a first array, measuring at least a second temporally variable contrast agent concentration in a second region of interest in an organ by determining a change in the CT values occurring there over a multiplicity of measurement times and saving the contrast agent profile $v_m(t)$ in at least a second array, temporally synchronizing the two arrays by interpolating the values of at least one array onto a prescribed time pattern, fitting a theoretical parameterized contrast agent profile $v_t(t)$ in the second region of the organ to the at least one contrast agent profile $v_m(t)$ measured in the second region of the organ by minimizing the differences between the theoretical and measured contrast agent profiles $|v_t(t)-v_m(t)|$ over a multiplicity of times in the measurement interval by fitting the function parameters, and determining at least one perfusion parameter from the obtained function parameters in the case of minimal deviation between the theoretical and measured contrast agent profiles $|v_t(t)-v_m(t)|$.

In the process, the function $$v_t(t) = v_0 + I_{in}\int_{-\infty}^{t} a(t' - t_{in})\,dt' - I_{out}\int_{-\infty}^{t} a(t' - t_{out})\,dt',$$

which has $v_0$, $t_{in}$, $t_{out}$, $I_{in}$, $I_{out}$ as parameters which need to be fitted, can be used as the theoretical contrast agent profile, with it being possible for the function $$\chi^2 = \sum_n (v_m(t_n) - v_t(t_n))^2$$

to be minimized for the fit.

In another refinement of at least one embodiment of the method, provision is made for the function $\chi^2 = VV - v_0 V - I_{in}VA_{in} + I_{out}VA_{out}$ to be minimized for the fit by only varying the parameters $A_{in}$ and $A_{out}$, the parameters $v_0$, $I_{in}$, and $I_{out}$ being calculated as a function of the parameters $A_{in}$ and $A_{out}$, with $$A_{in} = \int_{-\infty}^{t} a(t' - t_{in})\,dt',$$

$$A_{out} = \int_{-\infty}^{t} a(t' - t_{out})\,dt',$$

and $$V = \sum_n v_m(t_n).$$

In order to calculate the different perfusion parameters, the following relations between function parameter and function parameter can be applied and output:

blood flow $CBF = I_{in}$,
blood volume $CBV = I_{in}(t_{out} - t_{in})$
time to start $TTS = t_{in}$,
time to drain $TTD = t_{out}$, mean transit time MMT=$t_{out}-t_{in}$,
permeability=$I_{in}-I_{out}$ Furthermore, it is possible for a number of connected voxels in the lumen of an artery and their average contrast agent concentration to be considered and used as the first arterial region.

A single voxel or, in order to minimize the noise of the measurement data, a number of voxels and their average contrast agent concentration can be used as the second region in an organ.

It can be advantageous for the first region to comprise more voxels than the second region.

Temporally synchronizing the arrays can be oriented toward the times of the measurement points of the first region or toward the times of the measurement points of the second region, or it is also possible to use a prescribed time pattern with regular intervals to temporally synchronize the arrays. The method can be used very flexibly as a result of this very variable option for temporal synchronization.

Furthermore, it is advantageous for the first and second regions to be located at different z-positions of a system axis of the tomography system used. Also, the first and second regions should advantageously be located within the same organ.

The method according to at least one embodiment of the invention can be used in particular in x-ray CT systems and MRI systems, with zigzag helical scans being particularly suitable in connection with a CT scan.

BRIEF DESCRIPTION OF THE DRAWINGS

In the following text, at least one embodiment of the invention will be explained in more detail with the aid of the figures, with only features required for the understanding of the invention being illustrated. The following reference symbols are used: 1 to 4: profile curves of CT values in an organ after a bolus has been administered; 5: arterial influx into an organ; 6: organ; 7: venous efflux from an organ; 8: voxel in a region of interest of the organ; C1: CT-system/C-arm system; C2: first x-ray tube; C3: first detector; C4: second x-ray tube (optional); C5: second detector (optional); C6: gantry housing; C7: C-arm; C8: examination couch; C9: system axis; C10: control and computational unit with an additional EKG function; C11: contrast agent applicator; C12: EKG line; N1: MRI system; N2: magnetic coils; N3: receiving coils; N4: gradient coils; N6: housing; N10: control and computational unit; P: patient; $Prg_1$-$Prg_n$: programs; a(t): contrast profile in an arterial influx; c(t): contrast profile in one or more voxel(s) of an organ; v(t): contrast profile in a venous efflux.

In detail.

DETAILED DESCRIPTION OF THE EXAMPLE EMBODIMENTS

Figure 1:
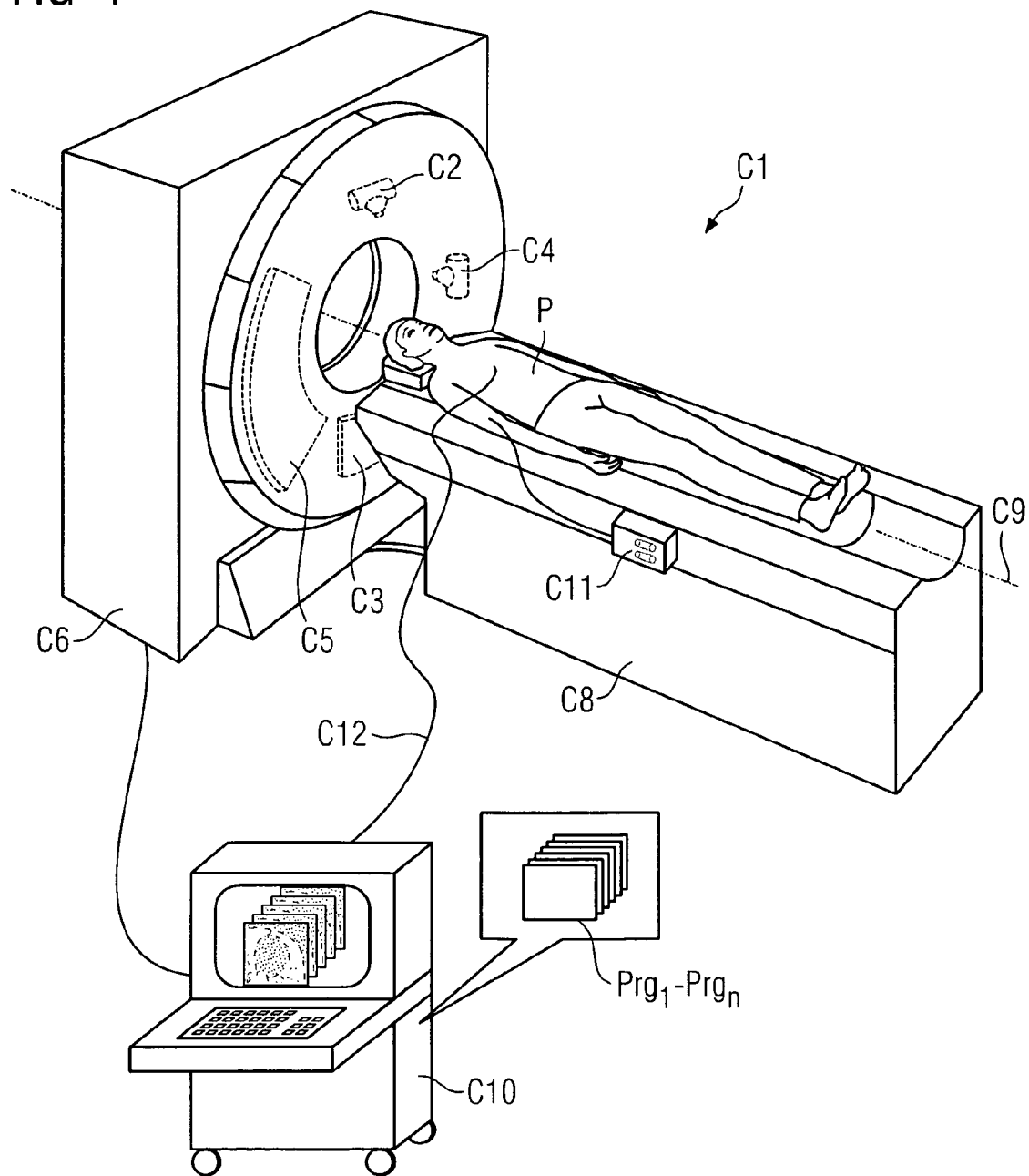
FIG. 1 shows a CT system for carrying out the method according to an embodiment of the invention.

Various example embodiments will now be described more fully with reference to the accompanying drawings in which only some example embodiments are shown. Specific structural and functional details disclosed herein are merely representative for purposes of describing example embodiments.

The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

By way of example, FIG. 1 shows a CT system C1 which can carry out the method according to an embodiment of the invention. The CT system C1 has a first tube/detector system comprising an x-ray tube C2 and a detector C3 lying opposite thereto. Optionally, this CT system 1 can include a second x-ray tube C4 with a detector C5 lying opposite thereto. Both tube/detector systems are located on a gantry which is arranged in a gantry housing C6 and rotates about a system axis C9 during the scan. The patient P is located on a displaceable examination couch C8 which is pushed—either continually or sequentially—along the system axis C9 through the scanning field located in a round opening in the gantry housing C6, with the attenuation of the x-ray radiation emitted by the x-ray tubes being measured by the detectors.

A contrast agent applicator C11 can be used to inject a contrast agent bolus into the patient P during the measurement so that the blood vessels can be made to be more visible or so that a perfusion measurement can be carried out. In the case of cardio-measurements, the cardiac activity can additionally be measured using an EKG line C12 and an EKG-gated scan can be effected.

The CT system is controlled using a control and computational unit C10 which comprises computer programs $Prg_1$ to $Prg_n$ that can execute the previously described method according to an embodiment of the invention. In addition, image data can also be output by way of this control and computational unit C10.

Figure 2:
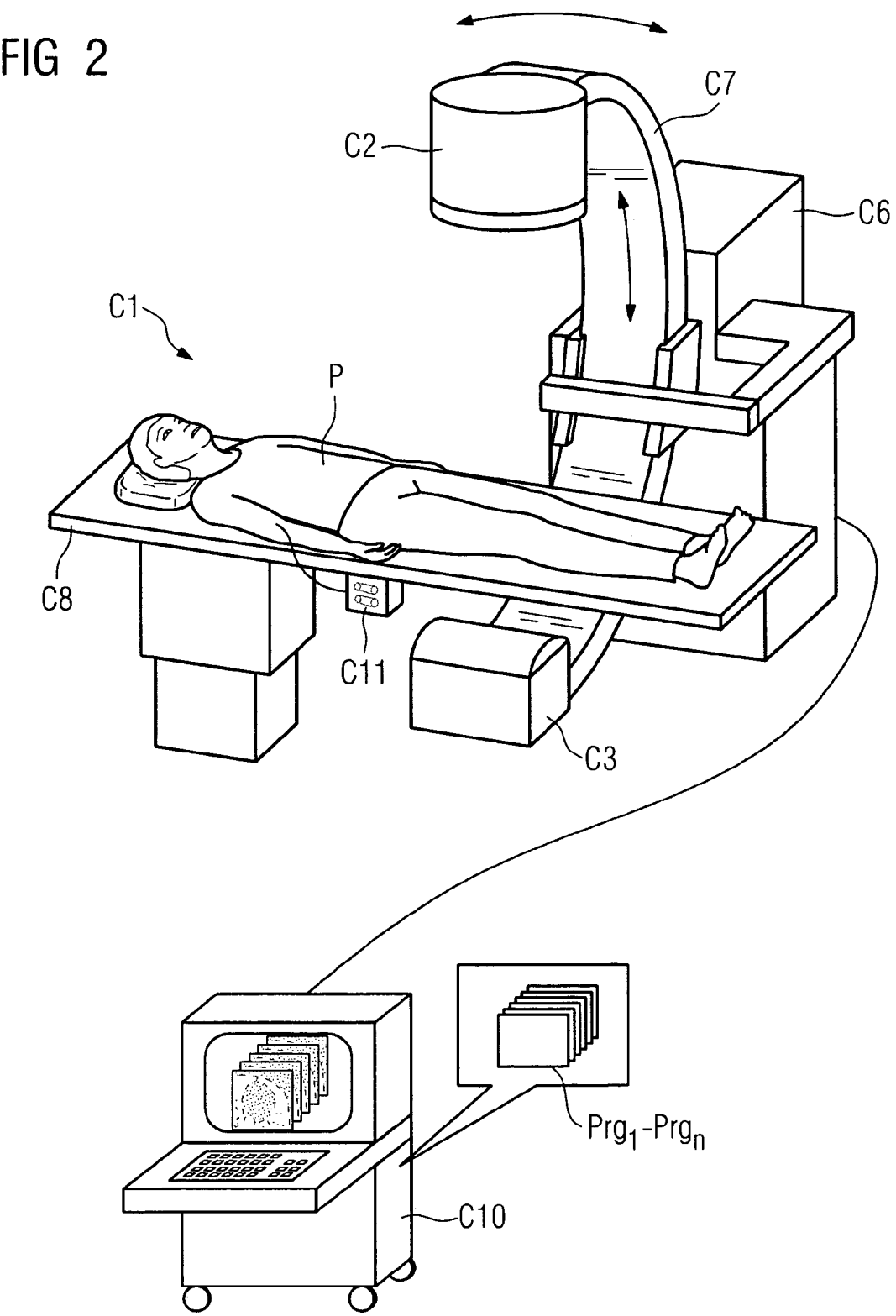
FIG. 2 shows a C-arm system for carrying out the method according to an embodiment of the invention.

Alternatively, this method can also be used in fluoroscopy. With respect to this, FIG. 2 shows a C-arm system C1 by which fluoroscopic images can be generated, in particular within the scope of interventional angiography. The C-arm system C1 illustrated here also comprises an x-ray tube 2 with a flat-panel detector C3 lying opposite thereto. Both systems can be pivoted to an arbitrary position about the patient P by way of a pivot arm C7. The patient P is located on a patient couch C8 which additionally comprises a contrast agent applicator system C11 in order to inject a contrast agent for imaging blood vessels where necessary. The system is controlled by a control and computational unit C10 which stores computer programs $Prg_1$ to $Prg_n$ that can also, inter alia, execute the method for image processing according to an embodiment of the invention.

Figure 3:
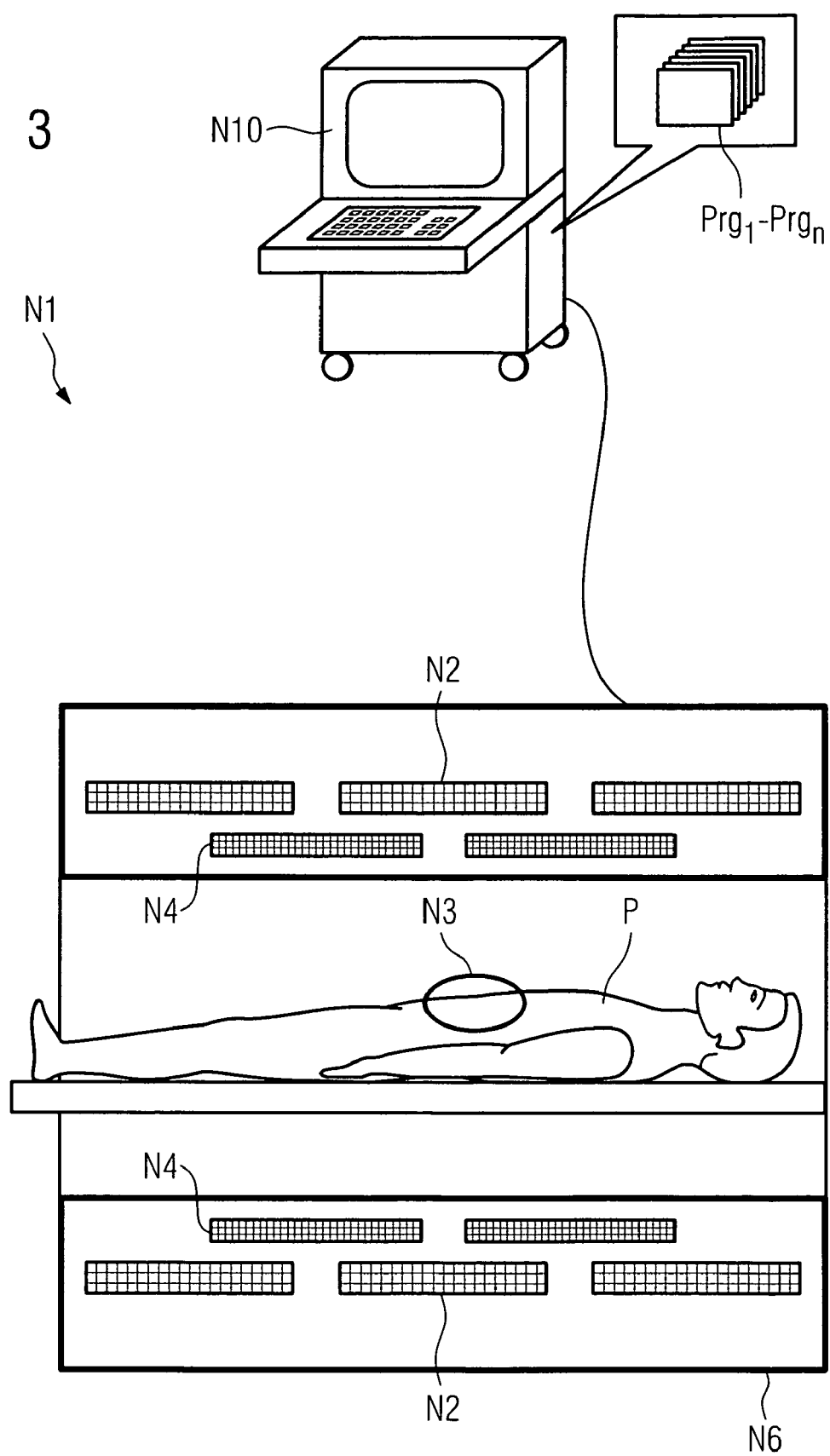
FIG. 3 shows an MRI system for carrying out the method according to an embodiment of the invention.

Finally, FIG. 3 schematically illustrates a magnetic resonance imaging system (MRI system) N1. In a housing N6, this MRI system N1 comprises magnetic coils N2 for generating a strong main magnetic field, as a result of which the hydrogen atoms in the body of the patient align parallel or anti-parallel to the magnetic field lines according to their spin. Excitation of these atomic nuclei using a variable electromagnetic field at the resonant frequency of the atomic nuclei causes the latter to oscillate. Once the excitation frequency has been switched off, the atomic nuclei again return to their position and emit their oscillation energy in the form of electromagnetic oscillation energy which is measured using receiving coils N3. Additional magnetic coils N4 generate a weak magnetic field with a defined field gradient, as a result of which the signals emitted by the nuclei contain location information by which the position of the emitted signal can be defined. The control of this system N1 and the evaluation of the measured signals are carried out by the control and computational unit N10 which stores programs $Prg_1$ to $Prg_n$ that execute the method according to an embodiment of the invention in addition to their control and image calculation functions.

The method according to an embodiment of the invention is a method for determining various perfusion parameters such as blood flow, blood volume, start times, and means transit time, with this method also intended to be capable of processing measurements at the same z-position which are recorded at intervals with differing lengths. For example, such situations arise when carrying out so-called zigzag scans in CT. Such perfusion measurements are not limited to CT and can also be carried out by MRI methods.

Figure 4:
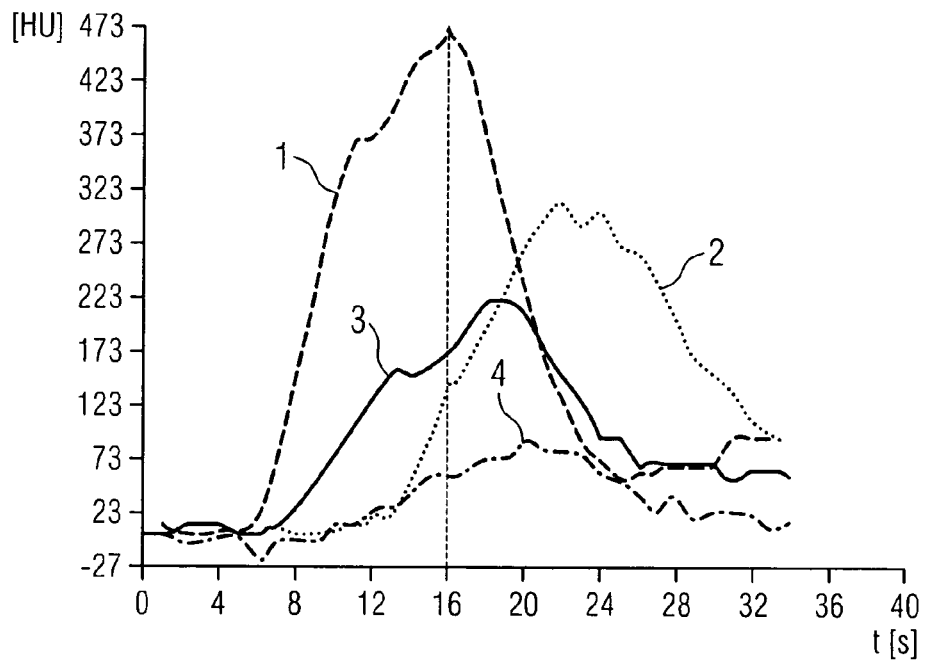
FIG. 4 shows measured contrast profiles in an organ.

During such a perfusion measurement, the concentration of a contrast agent, in particular in the arterial region and tissue region of an organ, is measured over a relatively long period of time at different locations within a patient, in particular in an organ of the patient, with the changes in concentration of a contrast agent over time being determined. By way of example, FIG. 4 shows such concentration curves which were recorded by a CT system at different locations after a contrast agent bolus was administered. For the sake of simplicity, the average CT values, which to a first approximation increases linearly with the concentration of the contrast agent, are plotted over time t at four locations which correspond to the curves 1 to 4. In this case, curve 1 corresponds to a sum of pixels/voxels in an organ-supplying artery, and the curves 2 to 3 represent different tissue regions of interest (ROIs) in the observed organ. That is to say, the contrast agent bolus is washed-in into the organ from the artery corresponding to the curve 1, distributes itself across the organ in accordance with curves 2 to 4, and is subsequently washed out again.

Figure 5:
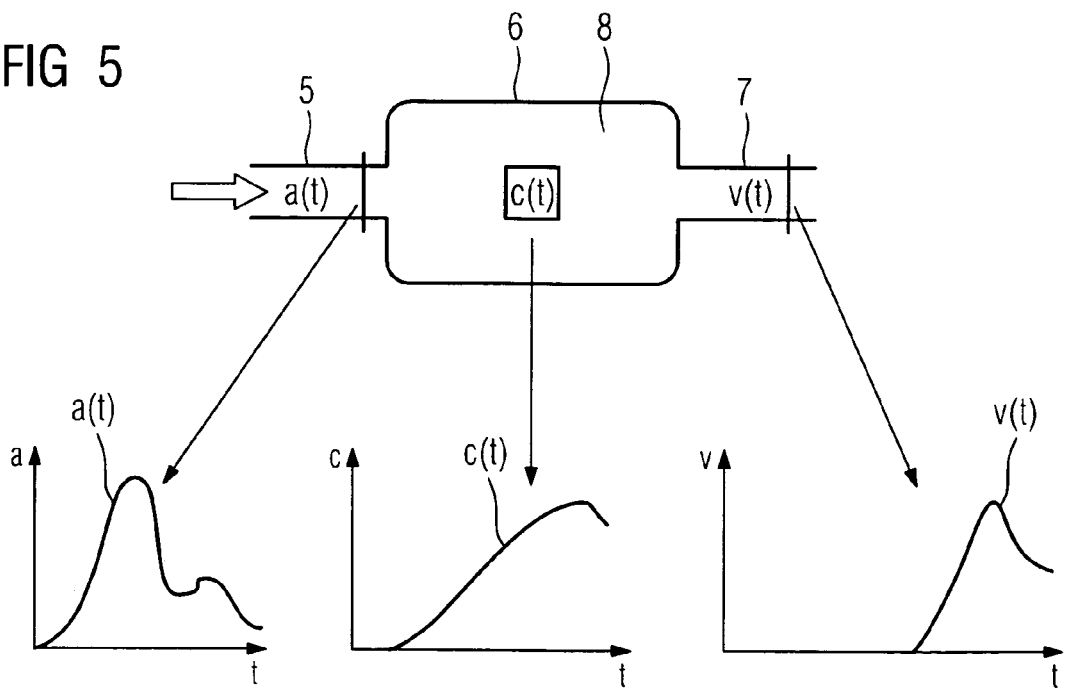
FIG. 5 shows a schematic illustration of the perfusion of an organ.

FIG. 5 schematically illustrates such a situation. Here, the organ 6 with the supply artery 5 and the deferent vein 7 are illustrated at the top. A region 8 is sketched in the organ which is intended to represent an observed ROI. The corresponding measured profiles of the contrast agent concentrations a(t), c(t), and v(t) in, respectively, the artery, organ tissue, and vein are shown in the three illustrations situated below which are connected with an arrow. From the transfer functions of the concentrations washing in and out relative to the tissue, medical statements about the function or the respective tissue or organ can be made in a known manner. In this case, the transfer function of the arterial region to the tissue part is essential, while the efflux of the contrast agent bolus is generally looked at less.

The following text is intended to show how perfusion parameters can be determined directly from the measured concentration curves in the arterial region and in the tissue. The following designations are used:

concentration curve in the aorta: a(t)

concentration curve at the location of the perfusion measurement: c(t)

Fourier transform $F(\omega)$ of a function $f(t)$:

$$F(\omega) = \int_{-\infty}^{\infty} e^{i\omega t} f(t) dt \qquad \text{Eq. 1}$$

inverse transform of F(ω) using an inverse Fourier transform to the function $f(t)$:

$$f(t) = \frac{1}{2\pi} \int_{-\infty}^{\infty} e^{-i\omega t} F(\omega) d\omega \quad \text{Eq. 2}$$

Classical Perfusion Calculation

In classical perfusion calculations, the blood flow CBF and blood volume CBV parameters are measured or calculated. The parameters can be represented by:

$$CBF = \frac{\text{Maximal slope}}{\text{Peak aortic enhancement}} = \frac{Max_t \partial_t c(t)}{Max_t a(t)} \quad \text{Eq. 3}$$

$$CBV = \frac{\text{Peak enhancement}}{\text{Peak aortic enhancement}} = \frac{Max_t c(t)}{Max_t a(t)} \quad \text{Eq. 4}$$

Perfusion by Deconvolution

The perfusion calculations by deconvolution assume that a tissue voxel behaves like a linear system. The concentration curve c(t) measured at a tissue voxel is calculated from the total contrast agent i(t) that has flowed into the system and the total contrast agent o(t) that has flowed out of the system again.

$$c(t) = \int_{-\infty}^{t} (i(t') - o(t')) dt' \quad \text{Eq. 5}$$

applies, which, in differential form can be expressed as $$\partial_t c(t) = i(t') - o(t'). \quad \text{Eq. 6}$$

In the following calculations, the assumption is made that the entire contrast agent that flows into the system flows out of it as well. Hence, the blood flow CBF into the voxel equals the blood flow out of the voxel, and $$\int_{-\infty}^{\infty} i(t) dt = \int_{-\infty}^{\infty} o(t) dt \quad \text{Eq. 7}$$

holds.

The area under c(t) represents the blood volume CBV. To this end, partial integration is utilized:

$$\int_{-\infty}^{\infty} c(t) dt = \int_{-\infty}^{\infty} \int_{-\infty}^{t} (i(t') - o(t')) dt' dt \quad \text{Eq. 8}$$

$$= t \int_{-\infty}^{\infty} \partial_t dt \int_{-\infty}^{t} (i(t') - o(t')) dt'$$

$$= t \int_{-\infty}^{t} i(t') - o(t') dt' \Big|_{-\infty}^{\infty} -$$

$$\int_{-\infty}^{\infty} t \partial_t dt \int_{-\infty}^{t} (i(t') - o(t')) dt'$$

$$= -\int_{-\infty}^{\infty} t(i(t') - o(t')) dt$$

$$= \int_{-\infty}^{\infty} t o(t) dt - \int_{-\infty}^{\infty} t i(t) dt$$

$$= MTT_0 \int_{-\infty}^{\infty} o(t) dt - MTT_i \int_{-\infty}^{\infty} i(t) dt,$$

where the mean transit time $MTT_f$ of a distribution $f(t)$ was defined as its first moment by $$MTT_f = \frac{\int_{-\infty}^{\infty} t f(t) dt}{\int_{-\infty}^{\infty} f(t) dt}. \quad \text{Eq. 9}$$

In the case of the linear system, the existence of a function $f(t)$ which maps the function i(t) on o(t) can be assumed, so that $$o(t) = \int_{-\infty}^{\infty} f(t - t') i(t') dt'. \quad \text{Eq. 10}$$

Under the assumption that the influx and efflux occur in the same region, the convolution kernel $f(t)$ can be normed, with $$\int_{-\infty}^{\infty} f(t) dt = 1, \quad \text{Eq. 11}$$

if its mean transit time corresponds to that of the system. When looking at the total tissue voxel, the following holds:

$$MTT_f = \int_{-\infty}^{\infty} t f(t) dt. \quad \text{Eq. 12}$$

The relation between blood volume CBV, mean transit time MTT and blood flow CBF is given by $$CBV = MTT \cdot CBF. \quad \text{Eq. 13}$$

If Eq. 10 is inserted into Eq. 5, the integration results in $$c(t) = \int_{-\infty}^{\infty} i(t') dt' \int_{-\infty}^{t-t'} (\delta^{(1)}(t'') - f(t'')) dt'' \quad \text{Eq. 14}$$

$$= \int_{-\infty}^{\infty} i(t') r(t - t') dt'. \quad \text{Eq. 15}$$

From this it is clear that it is not only the efflux o(t) which can be determined from the influx i(t) via a convolution, but also c(t) which has a convolution kernel r(t) given by $$r(t) = \int_{-\infty}^{t} (\delta^{(1)}(t') - f(t')) dt' = \theta(t) - \int_{-\infty}^{t} f(t') dt'. \quad \text{Eq. 16}$$

The convolution theorem specifies that this relation can be transformed into a simpler formula in Fourier space, namely $$C(\omega) = R(\omega) I(\omega). \quad \text{Eq. 17}$$

From this, r(t) can be calculated using $$r(t) = \int_{-\infty}^{\infty} e^{-i\omega t} \frac{C(\omega)}{I(\omega)} d\omega. \quad \text{Eq. 18}$$

Thus, a measured influx i(t) and a measured tissue curve c(t) can be used to determine the convolution kernel r(t) and, from this, f(t) via $$\partial_t r(t) = \delta^{(1)}(t) - f(t). \quad \text{Eq. 19}$$

Hence, the function f(t) contains all the information about the system, that is to say the examined voxel. The information relates to the reaction of the system to an unretarded impulse of a contrast agent, which cannot be effected in a normal examination.

A partial integration is used for r(t):

$$\int_{-\infty}^{\infty} r(t) \, dt = MTT_f. \quad \text{Eq. 19a}$$

Perfusion Model
Direct estimation by deconvoluting only provides unreliable results on account of the given data quality, i.e. signal-to-noise ratio. It is for this reason that the following further expedient approximations can be made with regard to the measured perfusion data.

Both the influx and efflux in each voxel have the same form as the function of the aorta. They are only shifted in time and varied in height:

$$i(t) = I_{in} a(t - t_{in}) \text{ and}$$

$$o(t) = I_{out} a(t - t_{out}). \quad \text{Eq. 20}$$

Hence, every voxel curve is fitted to the function $$v_t(t) = v_0 + I_{in} \int_{-\infty}^{t} a(t' - t_{in}) \, dt' - I_{out} \int_{-\infty}^{t} a(t' - t_{out}) \, dt', \quad \text{Eq. 21}$$

with $v_0$ corresponding to the level—for example, a CT value—without a contrast agent injection.

This corresponds to a system function r(t) which maps the influx onto the measured voxel curve $$f(t) = \frac{I_{out}}{I_{in}} \delta^{(1)}(t_{out} - t_{in} - t) \quad \text{Eq. 22}$$

$$= \frac{I_{out}}{I_{in}} \delta^{(1)}(MTT - t) \quad \text{Eq. 23}$$

or to a system function $$r(t) = \theta(t) - \frac{I_{out}}{I_{in}} \theta(MTT - t) \quad \text{Eq. 24}$$

which maps an input curve onto a tissue curve.

The parameters are estimated such that they are minimized, and $$\chi^2 = \sum_n (v_m(t_n) - v_t(t_n))^2 \quad \text{Eq. 25}$$

holds. Here, n is intended to represent the measurement times or the given time pattern points.

The minimum of $\chi^2$ is calculated by differentiating it with respect to the sought after parameters and setting the result to zero. Here, this is carried out for the parameters $v_0$, $I_{in}$, and $I_{out}$. Using the simplification $$A(t - t_{in}) = a \int_{-\infty}^{t} (t' - t_{in}) \, dt', \quad \text{Eq. 26}$$

$$\chi^2 = \sum_n (v_m(t_n) - v_t(t_n))^2 \quad \text{Eq. 27}$$

$$= \sum_n (v_m(t_n) - (v_0 + I_{in} A(t_n - t_{in}) - I_{out} A(t_n - t_{out})))^2$$

is obtained.

If the derivative with respect to $v_0$ is set to zero, i.e.

$$\frac{\partial \chi^2}{\partial v_0} = 0, \quad \text{Eq. 28}$$

$$\sum_n (v_m(t_n) - (v_0 + I_{in} A(t_n - t_{in}) - I_{out} A(t_n - t_{out}))) = 0 \quad \text{Eq. 29}$$

is obtained.

$I_{in}$ and $I_{out}$ are calculated accordingly:

$$\frac{\partial \chi^2}{\partial I_{in}} = 0 \quad \text{Eq. 30}$$

yields $$\sum_n (v_m(t_n) - (v_0 + I_{in} A(t_n - t_{in}) - I_{out} A(t_n - t_{out}))) A(t_n - t_{in}) = 0 \quad \text{Eq. 31}$$

and $$\frac{\partial \chi^2}{\partial I_{out}} = 0 \quad \text{Eq. 32}$$

yields $$\sum_n (v_m(t_n) - (v_0 + I_{in} A(t_n - t_{in}) - I_{out} A(t_n - t_{out}))) A(t_n - t_{out}) = 0. \quad \text{Eq. 33}$$

By rearranging the individual terms, and by using the following simplifications:

$$\sum_n v_m(t_n) = V \quad \text{Eq. 34a}$$

$$\sum_n A(t_n - t_{in}) = A_{in} \quad \text{Eq. 34b}$$

$$\sum_n A(t_n - t_{out}) = A_{out} \quad \text{Eq. 34c}$$

$$\sum_n v_m(t_n) A(t_n - t_{in}) = V A_{in} \quad \text{Eq. 34d}$$

$$\sum_n v_m(t_n) A(t_n - t_{out}) = V A_{out} \quad \text{Eq. 34e}$$

$$\sum_n A(t_n - t_{in}A(t_n - t_{in}) = AA_{inin} \qquad \text{Eq. 34f}$$

$$\sum_n A(t_n - t_{in}A(t_n - t_{out}) = AA_{inout} \qquad \text{Eq. 34g}$$

$$\sum_n A(t_n - t_{out}A(t_n - t_{out}) = AA_{outout}, \qquad \text{Eq. 34h}$$

the following system of equations is obtained:

$$V - nv_0 - I_{in}A_{in} + I_{out}A_{out} = 0$$

$$V - nv_0 - I_{in}A_{in} + I_{out}A_{out} = 0$$

$$VA_{out} - v_0 A_{out} - I_{in}AA_{inout}I_{out}AA_{outout} = 0, \qquad \text{Eq. 35}$$

which can be expressed as $$\begin{pmatrix} V \\ VA_{in} \\ VA_{out} \end{pmatrix} = \begin{pmatrix} n & A_{in} & A_{out} \\ A_{in} & AA_{inin} & AA_{inout} \\ A_{out} & AA_{inout} & AA_{outout} \end{pmatrix} \begin{pmatrix} v_0 \\ I_{in} \\ -I_{out} \end{pmatrix} \qquad \text{Eq. 36}$$

in matrix form. After inverting, the sought after parameters are obtained in terms of the voxel data:

$$\begin{pmatrix} v_0 \\ I_{in} \\ -I_{out} \end{pmatrix} = \frac{1}{\text{Det}} \begin{pmatrix} A & B & C \\ B & D & E \\ C & E & F \end{pmatrix} \begin{pmatrix} V \\ VA_{in} \\ VA_{out} \end{pmatrix}, \qquad \text{Eq. 37}$$

with the following simplifications:

$$A = AA_{outout}AA_{inin} - AA_{inout}^2 \qquad \text{Eq. 38a}$$

$$B = A_{out}AA_{inout} - A_{in}AA_{outout} \qquad \text{Eq. 38b}$$

$$C = A_{in}AA_{inout} - A_{out}AA_{inin} \qquad \text{Eq. 38c}$$

$$D = nAA_{outout} - A_{out}^2 \qquad \text{Eq. 38d}$$

$$E = A_{in}A_{out} - nAA_{inout} \qquad \text{Eq. 38e}$$

$$F = nAA_{inin} - A_{in}^2, \qquad \text{Eq. 38f}$$

and $$\text{Det} = nA + A_{in}B + A_{out}C \qquad \text{Eq. 39}$$

The advantage of this ansatz is that the inversion matrix only depends on the time structure of the voxel and the integration values of the aorta, but not on the precise absorption coefficient of the voxel in the CT. Thus, a single calculation of the elements of the inversion matrix suffices for all voxels in a slice, and a huge acceleration of the calculation is achieved.

The method described above analytically calculates the parameters $v_0$, $I_{in}$, and $I_{out}$. These parameters also depend on the parameters $t_{in}$ and $t_{out}$, which have to be determined by trial and error using Eq. 27. To put it simply, this can now be effected using the equation $$\chi_{min}^2 = VV - v_0 V - I_{in}VA_{in} + I_{out}VA_{out}, \qquad \text{Eq. 40}$$

where $$VV = \sum_n v_m(t_n) \cdot v_m(t_n).$$

This means that only two more parameters—specifically $A_{in}$ and $A_{out}$—have to be determined so that $\chi^2$ is minimized.

Once these two parameters $A_{in}$ and $A_{out}$ are determined, the following perfusion parameters can be calculated directly since all required parameters $I_{in}$, $I_{out}$, $t_{in}$, and $t_{out}$ are functions of $A_{in}$ and $A_{out}$. The following holds true:

$$\text{blood flow}(CBF) = I_{in}, \qquad \text{Eq. 41a}$$

$$\text{blood volume}(CBV) = I_{in}(t_{out} - t_{in}), \qquad \text{Eq. 41b}$$

$$\text{time to start}(TTS) = t_{in}, \qquad \text{Eq. 41c}$$

$$\text{time to drain}(TTD) = t_{out}, \qquad \text{Eq. 41d}$$

$$\text{mean transit time}(MMT) = t_{out} - t_{in}, \qquad \text{Eq. 41e}$$

$$\text{permeability} = I_{in} - I_{out}. \qquad \text{Eq. 41f}$$

Overall, a method prescription in accordance with the relationships described above can be effected as follows:

1) Measure the contrast agent profile a(t) in an artery or in one or more voxels of the artery.

2) Determine the integral of the contrast agent profile a(t), that is to say the area A(t) under the curve a(t). For example, this can be effected by interpolation and numerical integration.

3) Measure the contrast agent profile v(t) in one voxel or a number of voxels of an ROI at the times $t_n$ available from the images, and calculate VV and V.

4) A multiplicity of n times are assumed to be distributed arbitrarily over the measurement interval, i.e. from t=0 to t=$t_n$, and the values of $A_{in}$ and $A_{out}$ are calculated in accordance with equations 34b and 34c, in each case with equation 26, for these arbitrarily assumed times. Conveniently, equally spaced times can be selected, the frequency and distances between which determine the accuracy of the results.

5) The inversion matrix in accordance with equation 37 is subsequently generated using equations 38a-38f and equation 39.

6) Calculate $VA_{in}$ and $VA_{out}$ for all times from t=0 to t=$t_n$. Loop over all $t_{in}$ and $t_{out}$:

7) Determine the combination of values of $t_{in}$ and $t_{out}$ which lead to a minimum of $\chi^2$ in equation 40 by trial and error. To this end, the previously calculated combinations V, $VA_{in}$, and $VA_{out}$ can be used and $v_0$, $I_{in}$, and $I_{out}$ can be calculated using equation 37; these six variables and the possibly pre-calculated VV can be used in equation 40 to calculate the $\chi^2$ associated with this combination. This step 7) is carried out for all possible combinations of $t_{in}$ and $t_{out}$, and the smallest $\chi^2$ with the associated $t_{in}$ and $t_{out}$ is selected.

8) $VA_{in}$ and $VA_{out}$ can be defined using the values for $t_{in}$ and $t_{out}$ selected in this manner. Equation 37 then makes it possible to calculate $v_0$, $I_{in}$, and $I_{out}$. The value combinations for $t_{in}$, $t_{out}$, $v_0$, $I_{in}$, and $I_{out}$, calculated in this manner, then represent the optimally fitted values for the respective voxel or the respective voxel region.

Steps 3) to 8) have to then be carried out from scratch for every voxel.

9) Calculate the desired perfusion parameters from at least one of the equations 41a to 41f.

Reference is made to the fact that values which correspond to one another and at whose time no measurements are present can be determined using the method described here by interpolation from temporally adjacent measurement values.

The method described above is particularly advantageous in that all perfusion parameters including an MTT are determined using one model. Furthermore, measurement data at unequal time intervals can also be processed without problems. Furthermore, a single algorithm can be used to determine both neuro-perfusion and body-perfusion parameters. Finally, it is also possible to display voxel curves which correspond to individual voxels or voxel clusters for a more in-depth examination.

It is understood that the features of the invention mentioned above can be used not only in the respectively specified combination but also in other combinations or on their own without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product.

For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining at least one perfusion parameter in tomography, in which a contrast agent bolus, comprising a contrast agent, is dispensed to a patient while the patient is being scanned by a scanner, tomographic image series are reconstructed from a start time to an end time using absorption data scanned by the scanner, and at least one perfusion parameter, relating to diffusion of the contrast agent bolus, are calculated from the reconstructed tomographic image series using numerical modeling, the method comprising:

measuring a first temporally variable contrast agent concentration in a first arterial region by determining a change in scanned values occurring there over a multiplicity of measurement times and saving the measured first temporally variable contrast agent concentration as an arterial contrast agent profile in a first array;

measuring at least a second temporally variable contrast agent concentration in a second region of interest in an organ by determining a change in the scanned values occurring there over a multiplicity of measurement times and saving the measured at least a second temporally variable contrast agent concentration as a contrast agent profile in at least a second array;

temporally synchronizing the first and second arrays by interpolating the scanned values of at least one of the first and second arrays onto a prescribed time pattern;

fitting a theoretical parameterized contrast agent profile in the second region of the organ to the contrast agent profile measured in the second region of the organ by minimizing differences between the theoretical and measured contrast agent profiles over a multiplicity of times in the measurement interval by fitting function parameters; and determining at least one perfusion parameter from the function parameters in a case of minimal deviation between the theoretical and measured contrast agent profiles; wherein a function $$v_t(t) = v_0 + I_{in} \int_{-\infty}^{t} a(t' - t_{in}) dt' - I_{out} \int_{-\infty}^{t} a(t' - t_{out}) dt',$$

which has $v_0$, $t_{in}$, $t_{out}$, $I_{in}$, $I_{out}$ as parameters which need to be fitted, is used as the theoretical contrast agent profile, and a(t) corresponds to an arterial course of the contrast agent.

2. The method as claimed in claim 1, wherein a function $$\chi^2 = \sum_n (v_m(t_n) - v_t(t_n))^2 \text{ is}$$

is minimized for the fit, $v_m(t)$ being a measured contrast went profile for the second region.

3. The method as claimed in claim 1, wherein a function $\chi^2 = VV - v_0 V - I_{in} V A_{in} + I_{out} V A_{out}$ is minimized for the fit by only varying the parameters $A_{in}$ and $A_{out}$, the parameters $v_0$, $I_{in}$, and $I_{out}$ being calculated as a function of the parameters $A_{in}$ and $A_{out}$, with $$A_{in} = \int_{-\infty}^{t} a(t' - t_{in}) dt',$$

$$A_{out} = \int_{-\infty}^{t} a(t' - t_{out}) dt',$$

4. The method as claimed in claim 1, wherein a function parameter from among the function parameters represents blood flow CBF=$I_{in}$.

5. The method as claimed in claim 4, wherein a function parameter from among the function parameters represents blood volume CBV, and is determined according to CBV=$I_{in}$($t_{out}-t_{in}$).

6. The method as claimed in claim 1, wherein a function parameter from among the function parameters represents time to start TTS=$t_{in}$.

7. The method as claimed in claim 1, wherein a function parameter from among the function parameters represents time to drain TTD=$t_{out}$.

8. The method as claimed claim 1, wherein a function parameter from among the function parameters represents mean transit time MTT=$t_{out}-t_{in}$.

9. The method as claimed in claim 1, wherein a function parameter from among the function parameters represents permeability=$I_{in}-I_{out}$.

10. The method as claimed in claim 1, wherein the reconstructed tomographic image series includes a number of connected voxels in a lumen of an artery, and wherein the connected voxels and their average contrast agent concentration are used as the first arterial region.

11. The method as claimed in claim 1, wherein the reconstructed tomographic image series includes a number of voxels, and a single voxel from among the number of voxels is observed as the second region in an organ.

12. The method as claimed in claim 1, wherein the reconstructed tomographic image series includes a number of voxels, and wherein the voxels and their average contrast agent concentration are used as the second region in an organ.

13. The method as claimed in claim 1, wherein the reconstructed tomographic image series includes a number of voxels, and the first region comprises more voxels than the second region.

14. The method as claimed in claim 1, wherein temporally synchronizing the arrays is oriented toward the times of the measurement points of the first region.

15. The method as claimed in claim 1, wherein the temporally synchronizing the arrays is oriented toward the times of the measurement points of the second region.

16. The method as claimed in claim 1, wherein the prescribed time pattern with regular intervals is used to temporally synchronize the arrays.

17. The method as claimed in claim 1, wherein the first arterial region and the second region are located at different z-positions of a system axis of a tomography system used in the method.

18. The method as claimed in claim 1, wherein the first arterial region and the second region are located within the same organ.

19. The method as claimed in claim 1, wherein the scanner is magnetic resonance imaging (MRI) system.

20. The method as claimed in claim 1, wherein the scanner is a computed tomography (CT) system.

21. The method as claimed in claim 20, wherein CT values are used as the scanned values.

22. The method as claimed in claim 21, wherein the scan is effected as a zigzag helical scan.

23. The method as claimed in claim 20, wherein the scan is effected as a zigzag helical scan.

24. A tangible computer readable medium including program segments for, when executed on a computer device, causing the computer device to implement the method of claim 1.

25. A method for determining at least one perfusion parameter in tomography, the method comprising:

measuring an arterial contrast agent profile;

measuring a contrast agent profile in a tissue of an organ;

temporally synchronizing measured values of the arterial contrast agent profile and the contrast agent profile by interpolation;

fitting a theoretical parameterized contrast agent profile to the measured contrast agent profile in the tissue by minimizing differences between the theoretical and measured contrast agent profiles over a multiplicity of times in a measurement interval by fitting function parameters, the theoretical parameterized contrast agent profile being based on measured image values of the tissue of the organ without contrast; and determining the at least one perfusion parameter from the function parameters in the case of minimal deviation between the theoretical and measured contrast agent profiles; wherein
a function $$v_t(t) = v_0 + I_{in} \int_{-\infty}^{t} a(t' - t_{in}) dt' - I_{out} \int_{-\infty}^{t} a(t' - t_{out}) dt',$$

which has $v_0$, $t_{in}$, $t_{out}$, $I_{in}$, $I_{out}$ as parameters which need to be fitted, is used as the theoretical parameterized contrast agent profile, and a(t) corresponds to an arterial course of the contrast agent.

26. A tangible computer readable medium including program segments for, when executed on a computer device, causing the computer device to implement the method of claim 25.

* * * * *